United States Patent [19]
Koshi et al.

[11] Patent Number: 5,112,646
[45] Date of Patent: May 12, 1992

[54] APPARATUS FOR BIOLUMINESCENCE MEASUREMENT

[75] Inventors: Hiroyuki Koshi; Minoru Owada, both of Katsuta, Japan

[73] Assignee: Hitachi, Ltd., Tokyo, Japan

[21] Appl. No.: 658,441

[22] Filed: Jan. 28, 1991

Related U.S. Application Data

[63] Continuation of Ser. No. 230,080, Aug. 9, 1988, abandoned.

[30] Foreign Application Priority Data

Aug. 12, 1987 [JP] Japan .................... 62-199772

[51] Int. Cl.⁵ ............................................ G01N 21/76
[52] U.S. Cl. .................................... 422/52; 422/73; 436/52; 436/172; 435/291; 435/297; 435/298
[58] Field of Search ............ 422/52, 63, 68, 73; 436/52, 172; 435/291, DIG. 808, 297-301; 362/152, 154, 156; 206/569; 215/228; 220/212

[56] References Cited

U.S. PATENT DOCUMENTS

| | | | |
|---|---|---|---|
| 3,915,648 | 10/1975 | Stein | 422/52 |
| 3,950,637 | 4/1976 | Rodin | 362/154 |
| 3,977,836 | 8/1976 | Matsuda et al. | 422/83 |
| 4,101,383 | 7/1978 | Wyatt et al. | 435/808 |
| 4,301,252 | 11/1981 | Baker et al. | 435/290 |
| 4,594,646 | 6/1986 | Von Kohorn et al. | 362/154 |

OTHER PUBLICATIONS

Science, vol. 217 (1982), pp. 252-254.

Primary Examiner—Robert J. Warden
Assistant Examiner—Lyle A. Alexander
Attorney, Agent, or Firm—Antonelli, Terry, Stout & Kraus

[57] ABSTRACT

An apparatus for bioluminescence measurement, which measures a substance in vivo on the basis of bioluminescence, is provided with a device for supplying a reagent or buffer solution kept at a constant temperature in a thermostat tank to a container for culturing cells, so that the temperature of the container can be kept constant and the reagent or buffer solution in the container can be stirred.

11 Claims, 1 Drawing Sheet

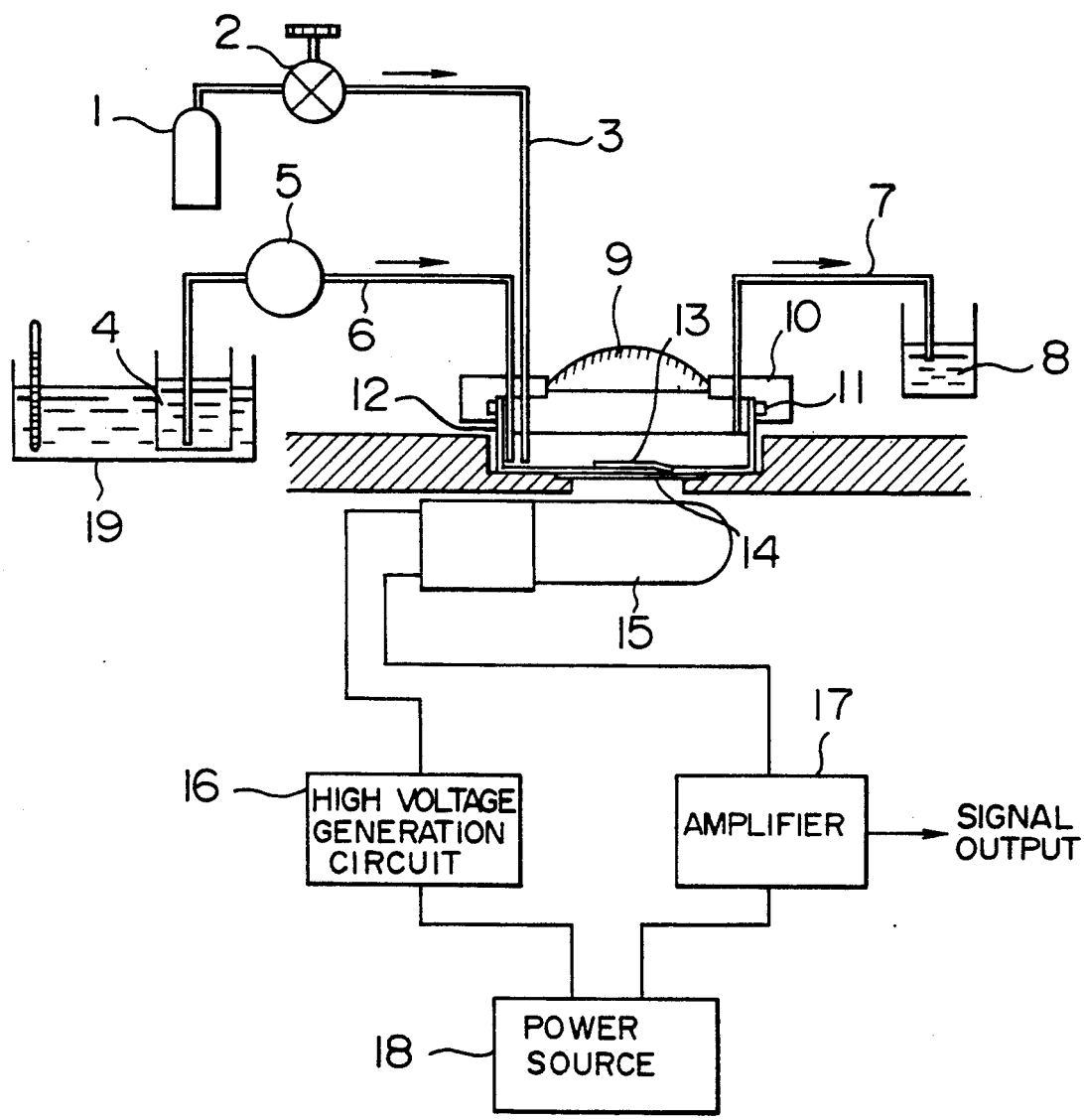

APPARATUS FOR BIOLUMINESCENCE MEASUREMENT

This application is a continuation of application Ser. No. 230,080, filed Aug. 9, 1988 now abandoned.

BACKGROUND OF THE INVENTION

This invention relates to an apparatus for measuring a substance in vivo on the basis of bioluminescence, and more particularly to an apparatus for bioluminescence measurement suitable for measuring an intracellular substance in smooth muscles.

A conventional apparatus for measuring a substance in vivo on the basis of bioluminescence is disclosed in Science, Vol. 217 (1982), pp 252-254.

Intracellular $C_a^{2+}$ is a fundamental factor for controlling the entire cell activity and recently relations between changes in $C_a^{2+}$ concentration and various cellular functions have been extensively studied.

Several procedures have been proposed for the measurement of $C_a^{2+}$, and one of the procedures is based on bioluminescence, using aequorin, a photoprotein. This procedure based on the bioluminescence is regarded as the most sensitive among the now available procedures.

Measurement of intracellular $C_a^{2+}$ concentration was initially directed to suspended cells as being the most easily measurable ones, where a cell suspension containing about $10^6$ cells/ml was subjected to measurement of the concentration. As regards cells with tissues, the cells were freed from the tissues by decomposition and then brought into a suspended state, followed by the measurement of the concentration, because the aim of the initial research was to find whether changes in the concentration of intracellular $C_a^{2+}$ could be brought about by an external stimulus or not, rather than to find the relations between changes in the concentration and various cellular functions.

With increasing necessity for more accurate measurement of changes in the concentration, the measurement based on the decomposition of tissues has not been maintained, because the cellular activities are naturally influenced with adjacent cells.

Recently, a procedure for propagating cells on a glass plate and placing the glass plate in a cubic cell has been employed. Furthermore, another procedure has been proposed, where cells are propagated on the surface of a small sphere, and measurement is made of the small sphere by suspending it in a cell. However, these procedures present a difficulty in the preparation and handling of a sample.

Heretofore, a Petri dish has been usually used for cell culturing and is easiest to handle for the cell culturing. Thus, if such a dish can be set directly in the sample section in a luminescence-measuring apparatus after the incubation, a more precise measurement can be made with simpler cell culturing. However, temperature control is a problem in using the Petri dish. One of the reasons for selecting the measurement of cells cultured on the surface of a small sphere is this temperature control. Observation of cellular activities in vivo must be made under the same conditions as in vivo as much as possible, and thus the sample temperature must be kept constant at 37° C. Thus, a sample container is usually set in a thermostat cell holder and a magnetic stirrer is placed in the cell to make the measurement with stirring. The stirring is indispensable for making the temperature constant in the sample cell. However, the stirrer cannot be used in the Petri dish, because it will peel the attached cells from the surface of the dish.

SUMMARY OF THE INVENTION

An object of the present invention is to provide an apparatus for bioluminescence measurement with a Petri dish.

The object of the present invention can be attained by supplying a reagent or a buffer solution kept at a constant temperature by a thermostant tank, etc. to a container in which cells are to be cultured.

By supplying a reagent or a buffer solution kept at a constant temperature to a container for culturing, the temperature of the container can be kept constant and the reagent or the buffer solution in the container can be stirred, and there is no fear of damaging the cells. Furthermore, the extracellular liquid can be constantly washed by supplying and discharging the reagent or the buffer solution to and from the container, respectively.

BRIEF DESCRIPTION OF THE DRAWING

Single FIGURE shows one embodiment of the present invention as applied to an apparatus for measuring intracellular $C_a^{2+}$.

DESCRIPTION OF THE PREFERRED EMBODIMENT

One embodiment of the present invention will be described in detail below, referring to the accompanying drawing, where the present invention is applied to an apparatus for measuring a concentration of intracellular $C_2^{2+}$ in vivo on the basis of aequorin, a photoprotein. Intracellular $C_a^{2+}$ in vivo is indispensable for controlling various cellular activities, and it is essential to clarify causes for the entire activity in vivo and diseases by measuring changes in $C_a^{2+}$ concentration with stimuli to the cells due to the measurement of $C_a^{2+}$ concentrations, and above all the measurement based on bioluminescence is most sensitive.

Cells 13 to be measured are cultured or introduction of aequorin into the cells is carried out in a Petri dish 12, usually 35 mm in diameter and 10 mm deep. The Petri dish 12 is set in an measurement apparatus having a receptor 20 with a recess hole for receiving the dish, and a lid 10 is placed on the dish 12. The lid 10 is provided with an O-ring 11 to tightly seal the dish inside. The lid 10 is also provided with a tube 6 for injecting a reagent or a buffer solution 4 for cell stimulation. The reagent or buffer solution 4 is controlled to a constant temperature in a thermostat tank 19 and injected into the dish 12 through a pump 5. In order to replace the reagent or buffer solution in the dish 12, the lid 10 is further provided with a tube 7 for discharging the reagent or buffer solution. Since the dish inside is tightly sealed with the O-ring 11, the reagent or buffer solution in the dish 12 is automatically discharged therefrom through the tube 7 as a waste solution, when the reagent or buffer solution 4 kept at a constant temperature is injected into the dish 12 through the pump 5, whereby the inside of the dish 12 can be kept at a constant temperature. In order to keep the pH of the reagent in the dish 12, a tube 3 for injecting a $CO_2$ gas (5%) 1 is provided through the lid 10. The gas pressure is controlled by a valve 2. Luminescence from the cells 13 passes through a window 14 provided at a portion of the recess hole and its intensity is measured by a photomultiplier 15. The luminescence is emitted in all directions from the cells 13, and a mirror 9 for focusing the upwardly directed luminescence onto the photomultiplier 15 is provided on the lid 10. The mirror 9 particularly has a vapor-deposited surface as an upper surface, as shown in the drawing, so that foulings, when formed from the reagent, etc. on the mirror bottom, can be simply removed therefrom. A high voltage to the photomultiplier 15 is supplied from a high voltage generation circuit 16. The output signal from the photomultiplier 15 is led to a amplifier 17 and the output signal from the amplifier 17 is led to a recorder or a computer (not shown in the drawing). Power is supplied to the high voltage generation circuit 16 and the amplifier 17 from a power source 18.

According to the foregoing embodiment of the present invention, a dish for culturing or pretreatment is directly set in a measurement apparatus, and thus there is no necessity for transplanting the cells, whereby deterioration of cells can be prevented. By providing a mirror on the lid, the measurement of bioluminescence can be made with a high sensitivity. Furthermore, by recovering the reagent or buffer solution as a waste solution 8, substances discharged from the cells into the reagent or buffer solution can be determined at the same time by some appropriate analytical means.

In the foregoing embodiment, a Petri dish is used, but can be replaced with a test tube, a cubic cell, etc. Furthermore, the pump 5 and the tube 6 can be replaced with other separating system such as a liquid chromatograph, etc. to conduct the pretreatment of the reagent to be added to the cells. In the foregoing embodiment, the window 14 is to prevent leakage of the reagent, etc. into the photomultiplier 15, and can be replaced with a spectrophotographic means such as an interference filter, etc.

According to the present invention an operation of transplanting the cultured cells into another container is unnecessitated after the pretreatment of a sample, thereby preventing deterioration of the sample and increasing the measurement accuracy.

What is claimed is:

1. An apparatus for bioluminescence measurement comprising:
   container means for containing a sample of cells to be cultured therein, said container means being a light transmissible culturing dish containing cultured cells and including at least an opening on an upper portion thereof;
   receptor means having a recess hole for receiving the culturing dish therein;
   a light-transmissible window being provided at a portion of the recess hole lower than a bottom portion of said culturing dish;
   lid means removably attached to said culturing dish for forming a closed chamber together with said culturing dish, said closed chamber being a gas-tight chamber which encloses said sample;
   a light-focusing mirror formed on said lid means for focusing luminance from said sample;
   first tubular means fixed to said lid means and extending into said closed chamber for discharging a portion of a liquid in said closed chamber;
   second tubular means fixed to said lid means and extending into said closed chamber for supplying at least one of a reagent solution and a buffer solution to said chamber;
   mean for supplying said at least one of a reagent solution and a buffer solution to said closed chamber through said second tubular means, thereby enabling culturing of said sample in said closed chamber, said supplying means including means for maintaining said solution at a constant temperature which is equal to the temperature inside said closed chamber; and
   means for detecting luminescence from said sample of cells in said closed chamber as focused by said light-focusing mirror and passing through said light-transmissible window.

2. An apparatus according to claim 1, wherein said detecting means is provided at a position lower than a flat bottom portion of said culturing dish.

3. An apparatus according to claim 1, wherein said light-focusing mirror and said detector means are oppositely arranged with each other with a flat bottom portion of said culturing dish being interposed therebetween.

4. An apparatus according to claim 1 wherein said culturing dish is a Petri dish.

5. An apparatus according to claim 1, wherein said light-focusing mirror is disposed on an interior surface of said lid means.

6. An apparatus according to claim 1, wherein said lid means is provided with a means for supplying a $CO_2$ gas to said closed chamber.

7. An apparatus according to claim 4, wherein said means for supplying a $CO_2$ gas to said closed chamber includes a third tubular means fixed to said lid means and extending into said closed chamber for discharging the $CO_2$ gas into said closed chamber.

8. An apparatus for bioluminescent measurement comprising:
   container means for containing a sample of a living body therein, said container means being a light-transmissible culturing dish containing cultured cells of said sample;
   receptor means having a recess hole for receiving said culturing dish therein;
   a light transmissible window provided at a portion of the recess hole lower than a bottom portion of said culturing dish;
   means for supplying and discharging fluid into and out of said culturing dish for enabling culturing of said sample in said culturing dish, said means for supplying and discharging fluid including first and second tubular members;
   lid means removably attached to said container means for forming a closed chamber together with said culturing dish, said lid means having at least one light-focusing mirror disposed on a surface thereof for focusing luminescence from said sample, said first and second tubular members being fixed to said lid means; and
   means for detecting said luminescence from said sample of cells in said closed chamber, said detecting means being disposed adjacent to said culturing dish for detecting said luminescence through a portion of said culturing dish as focused by said at least one light-focusing mirror and passing through said light-transmissible window.

9. An apparatus according to claim 8, wherein said container means comprises a Petri dish and said detecting means detects said luminescence through a flat bottom portion of said Petri dish.

10. An apparatus according to claim 8, further comprising a third tubular member fixed to said lid means for supplying a $CO_2$ gas to said closed chamber.

11. An apparatus according to claim 8, wherein said light-focusing mirror is disposed on an interior surface of said lid means.

* * * * *